United States Patent [19]

McGuire et al.

[11] Patent Number: 5,817,650
[45] Date of Patent: *Oct. 6, 1998

[54] TREATMENT OF SYSTEMIC LUPUS ERYTHEMATOSUS WITH DEHYDROEPIANDROSTERONE

[75] Inventors: James L. McGuire, deceased, late of Stanford, Calif.; Linda R. McGuire, administratrix, Westboro, Mass.; Ronald F. Van Vollenhoven; Edgar G. Engleman, both of Stanford, Calif.

[73] Assignee: The Board of Trustees of the Leland Stanford Junior University, Stanford, Calif.

[ * ] Notice: The term of this patent shall not extend beyond the expiration date of Pat. No. 5,567,696.

[21] Appl. No.: 833,338

[22] Filed: Apr. 4, 1997

Related U.S. Application Data

[63] Continuation of Ser. No. 958,911, Oct. 9, 1992.

[51] Int. Cl.$^6$ .................................................. A61K 31/56
[52] U.S. Cl. ............................................ 514/170; 514/171
[58] Field of Search ...................................... 514/170, 171

[56] References Cited

U.S. PATENT DOCUMENTS

| | | | |
|---|---|---|---|
| 4,628,052 | 12/1986 | Peat .......................................... | 514/178 |
| 5,001,119 | 3/1991 | Schwartz et al. ...................... | 514/178 |
| 5,567,696 | 10/1996 | McGuire et al. ...................... | 514/178 |

OTHER PUBLICATIONS

Katcher et al., "Applied Therapeutics The Clinical Use of Drugs", third edition, published by Applied Therapeutics, Inc. (Spokane WA), pp. 1433–1439, 1983.

Van Wollenhoven, R. P., et al. "Treatment of Systemic Lupus Erythematosus with Dehydroepiandrosterone, A Pilot Study", Arthritis and Rheumatism, Abstract No. 126, 35(9)S55, 1992.

Vande Weile, et al., "Studies on the Secretion and Interconversation of the Androgens", College of Physicians and Surgeons of Columbia University, pp. 275–305, (1963).

Steinberg, et al., "Approach to the Study of the Role of Sex Hormones in Autoimmunity," Arthritis and Rheumatism, vol. 22, No. 11, pp. 1170–1176, (Nov. 1979).

Roubinian, et al., "Danazol's Failure to Suppress Autoimmunity in NZB/NZW F1 Mice," Arthritis and Rheumatism, vol. 22, No. 12, pp. 1399–1402 (Dec. 1979).

Jungers, et al., "Low Plasma Androgens in Women with Active or Quiescent Systemic Lupus Erythematosus," Arthritis and Rheumatism, vol. 25, No. 4, pp. 454–457 (Apr. 1982).

Alcocer–Varela, et al., "Deceased Production of and Response to Interleukin–2 by Cultured Lymphocytes from Patients with Systemic Lupus Erythematosus," Journal of Clinical Investigation, vol. 69, pp. 1388–1392 (Jun. 1982).

Linker–Israeli, et al., "Defective Production of Interleukin 1 and Interleukin 2 in Patents with Systemic Lupus Erythematosus (SLE)," The Journal of Immunology, vol. 130, No. 6, pp. 2651–2655 (Jun. 1983).

Lahita, et al., "Increased Oxidatioin of Testosterone in Systemic Lupus Erythematosus," Arthritis and Rheumatism, vol. 26, No. 12, pp. 1517–1521 (Dec. 1983).

Murakawa, et al., "Characterization of T Lymphocyte Subpopulations Responsible for Deficient Interleukin 2 Activity in Patients with Systemic Lupus Erythematosus," The Journal of Immunology, vol. 134, No. 1, pp. 187–195 (Jan. 1985).

Lucas, et al., "Prevention of Autoantibody Formation and Prolonged Survival in New Zealand Black/New Zealand White F1 Mice Fed Dehydroisoandrosterone," The Journal of Clinical Investigation, vol. 75, pp. 2091–2093 (Jun. 1985).

Barrett–Conner, et al., "A Prospective of Dehydroepiandrosterone Sulfate, Mortality and Cardiovascular Disease," The New England Journal of Medicine, vol. 315, No. 24, pp. 1519–1524 (Dec. 1986).

Lahita, et al., "Low Plasma Androgens in Women with Systemic Lupus Erythematosus," Arthritis and Rheumatism, vol. 30, No. 3, pp. 241–248 (Mar. 1987).

Regelson, et al., "Hormonal Intervention: 'Buffer Hormones' or 'State Dependency'," Annals of the New York Academy of Sciences, vol. 521, pp. 260–273 (1988).

West, et al., "Danazol for the Treatment of Refractory Autoimmune Thromobcytopenia in Systemic Lupus Erythematosus," Annals of Internal Medicine, vol. 108, pp. 703–706 (1988).

Cottran, et al., "Altered Lipid Metabolism and Induction of Peroxisomal Activity in NZB/W Mice Fed a Diet Containing 0.45% Dehydroisoandrosterone (DHA)," The Journal of Cell Biology, Abstract No. 684, vol. 107, No. 6: 122A (Dec. 1988).

Matsunaga, et al., "Effects of Dehydroisoandrosterone (DHA) Administration on Macrophage Function and Spleen Cell Mitogenic Response in NZB/W Female Mice," The Faseb Journal, Abstract No. 4371, vol. 2, No. 5: A1048 (Mar. 1988).

Matsunaga, et al., "Dehydroepiandrosterone Prevention of Autoimmune Disease in NZB/W F$^1$ Mice: Lack of an Effect on Associated Immunological Abnormalities," Biochimica et Biophysica Acta, vol. 992, pp. 265–271 (1989).

Risdon, et al., "Mechanisms of Chemoprevention by Dietary Dehydroisoandrosterone: Inhibition of Lymphopoiesis," American Journal of Pathology, vol. 136, No. 4, pp. 759–769 (Apr. 1990).

(List continued on next page.)

Primary Examiner—Raymond Henley, III
Attorney, Agent, or Firm—Peter J. Dehlinger; Carol A. Stratford

[57] ABSTRACT

Systemic lupus erythematosus (SLE) is treated with dehydroepiandrosterone or its metabolite, sulfate ester, by itself or in combination with other therapies. Substantial improvement in SLE patients is observed during the course of treatment.

9 Claims, No Drawings

OTHER PUBLICATIONS

Gutierrez–Ramos, et al., "Recovery from Autoimmunity of MRL/lpr Mice After Infection with an Interleukin–2/Vaccinia Recombinant Virus," *Nature*, vol. 346, pp. 271–274 (Jul. 1990).

Lahita, et al., "Experience with 19–Nortestosterone in the Therapy of Systemic Lupus Erhythematosus: Worsened Disease after Treatment with 19–Nortestoterone in Men and Lack of Improvement in Women," *The Journal of Rheumatology*, vol. 19, No. 4, pp. 547–555 (1992).

Van Wollenhoven, et al., "Treatment of Systemic Lupus Erythematosus with Dehydroepiandrosterone: Follow–Up from an Open–Label Clinical Trial," *Arthritis and Rheumatism*, Abstract No. C241, 36(9): S228 (1993).

Van Wollenhoven, et al., "Treatment of Systemic Lupus Erythematosus with Dehydroepiandrosterone: Interim Analysis of Double–Blinded Randomized, Placebo–Controlled Clinical Trial," *Arthritis and Rheumatism*, Abstract No. 322, 36(9): S92 (1993).

TREATMENT OF SYSTEMIC LUPUS ERYTHEMATOSUS WITH DEHYDROEPIANDROSTERONE

This application is a continuation of application Ser. No. 07/958,911 filed Oct. 9, 1992.

TECHNICAL FIELD

The field of this invention concerns the treatment of systemic lupus erythematosus.

BACKGROUND

Systemic lupus erythematosus (SLE) is a debilitating autoimmune disease. Patients with SLE manifest various immunological abnormalities which probably reflect the immunopathological processes occurring concurrently in this multi-system disease. One consistent finding appears to be defective IL-2 production by peripheral blood T-lymphocytes which is independent of age or overall disease activity (Alcocer-Varela and Alarcon-Segovia, *J. Clin. Invest.* (1982), 69, 1388; Linker-Israeli, et al., *J. Immunol.* (1983), 130, 2651; Murakawy, et al., ibid (1985), 134, 187). The precise pathological significance of this is unknown. The administration of IL-2 in the murine lupus-like model MRL/lpr attenuated the autoimmune disease (Gutierrez-Ramos, *Nature* (1990), 346, 27). The sex hormone status of patients with SLE suggests that there is a relative deficiency of androgens (Jungers, et al. *Arthritis Rheum.* (1982), 25, 454; Lahita, et al. ibid (1983), 26, 1517). The administration of the androgen Danazol to patients with SLE, based on the proposition that there may be a protective effect conferred by androgens, has produced variable benefits with respect to disease activity and autoantibody production (Steinberg, et al., *Arthritis Rheum.* (1979), 22, 1170; Roubinian, et al., ibid (1979), 22, 1399).

Dehydroepiandrosterone (DHEA) is a natural androgen that is an intermediate in the synthetic pathway of cholesterol to testosterone and it is the most abundant secretory product of human adrenal glands (Vande Wiele, et al. *Recent Prog. Horm. Res.* (1963), 19, 275). About 30 mg/day of DHEA is produced by the adrenal glands in the form of the inactive sulfate ester and DHEA serum levels show a striking age-related decline (Barrett-Connor, et al. *New Engl. J. Med.* (1986), 315, 1519). DHEA has up-regulatory effects on IL-2 production by stimulating human T-cells in vitro. In the NZB/W mouse DHEA was found to profoundly delay the appearance of anti-DNA antibodies as well as the onset of nephritis and to prolong life (Lucas, et al. *J. Clin. Invest.* (1985), 75, 2091). There have also been reports that the administration of DHEA to MRL/lpr mice with severe lupus-like disease resulted in dramatic reversal of disease activity.

There is, therefore, substantial interest in evaluating the use of DHEA or derivatives thereof as a medication for the treatment of SLE in humans, by itself or in combination with other drugs.

Relevant Literature

Regelson, et al., *Ann. N.Y. Acad. Sci.* (1988), 521, 260–273 provides a review of DHEA properties and uses. U.S. Pat. No. 4,628,052 claims the use of DHEA in the treatment of arthritis.

SUMMARY OF THE INVENTION

DHEA, metabolites, or derivative thereof is administered to SLE patients at a level to enhance the normal blood level by at least about 10%. One or more doses may be administered daily to maintain the desired concentration, where the DHEA may be administered in conjunction with other drugs conventionally used for the treatment of SLE. The treatment may be continuous, intermittent, or associated with episodic events.

DESCRIPTION OF THE SPECIFIC EMBODIMENTS

Systemic lupus erythematosus (SLE) patients are treated with a therapy comprising dehydroepiandrosterone (DHEA) or a derivative thereof, optionally in combination with other drug regimens employed for the treatment of SLE. For the most part, DHEA or the metabolite DHEA sulfate will be employed, individually or in combination, where the sulfate will be present as a physiologically-acceptable salt.

The DHEA may be administered in a variety of ways, orally, parenterally, or inhalation. For injection, the DHEA may be injected subcutaneously, intraperitoneally, intravascularly, etc. Depending upon the manner of introduction, the DHEA may be formulated in a variety of ways. The proportion of therapeutically active to carrier substance may vary from about 0.5–100 wt. %. The compositions can be prepared in various pharmaceutical forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include vegetable and animal oils and fats. Stabilizing agents, wetting and emulsifying agents, salts for varying the osmotic pressure or buffers for securing an adequate pH value, and skin penetration enhancers can be used as auxiliary agents.

For oral use, the pharmaceutical composition will generally contain from about 5–100% by weight of the active material. For other uses, the composition will generally have from about 0.5–50 wt. % of the active material.

Various carriers include excipients, tocopherol, dimethyl sulfoxide, etc.

The subject compositions will generally be administered daily, in an amount to provide at least about a 10%, usually at least about 25%, increase in the blood level of DHEA. Generally, the total daily dosage will be at least about 10 mg, usually at least about 25 mg, preferably about 50 mg, and not more than about 500 mg, usually not more than about 250 mg. The amount may vary with the general health of the patient, the response of the patient to the drug, whether the DHEA is used by itself or in combination with other drugs, and the like. Daily administrations may be one or more times, usually not more than about four times, particularly depending upon the level of drug which is administered.

Other drugs which may be used in accordance with conventional treatments include non-steroidal anti-inflammatory drugs, antimalarials, glucocorticosteroids, etc. These drugs include hydroxychloroquine, prednisone, quinacrine, azathioprine, etc. Dosage for prednisone will generally be from about 1–15, more usually from about 1–12 mg/day. The additional drugs may be administered separately or in conjunction with DHEA and may be formulated in the same formulation with DHEA.

The following examples are offered by way of illustration and not by way of limitation.

EXPERIMENTAL

The following study was performed. Eight female premenopausal SLE patients with mild to moderate disease were given DHEA 200 mg/day, open label for 3 months, while allowing changes in other medications to be made as clinically indicated. After 3 months, the SLE-disease activity index score (SLE-DAI) had improved by a clinically-significant margin in 5 patients, was unchanged in 2, and had worsened in 1 patient. Of 5 patients who were on prednisone at onset, 3 were able to significantly reduce the dose during the trial (average daily dose of the 5 patients on prednisone: 19.0 mg at onset vs. 13.6 mg after 3 months on DHEA). 7 patients reported a beneficial effect on general well-being, energy level or fatigue, and 5 had significant improvement as determined by a visual analog scale. Physicians' overall assessment of these patients was improved in 5 and unchanged or mixed in 3 patients. Side effects of DHEA in this trial included a transient increase in libido, a transient change in taste perception (1 patient) and mild to moderate acneiform dermatitis. During the 3 months of DHEA therapy, overall, favorable results were seen.

The following tables provide the patient profiles (Table 1), a summary of the outcome measures (Table 2), the tolerance and side effects (Table 3), and medication profiles (Table 4).

TABLE 1

Patient profiles.

| | Age | Ethnicity | SLE | Prior Manifestations | Manifestions at Enrollment |
|---|---|---|---|---|---|
| SB | 36 | C | 4 yr | LCV, thrombocytopenia, arthritis, fatigue, pleuritis OU, (+) FANA | Thrombocytopenia, fatigue, vasculitic skin lesions |
| SP | 38 | C | 15 yr | MR, OU, alopecia, LAN, arthritis, serositis, fever, CNS, (+) FANA | Arthritis, headaches |
| DW | 43 | C | 4 mo | Myalgias, arthritis, MR, photosensitive rash, fatigue, (+) FANA, (+) αDNA | Arthritis, myalgias, fatigue |
| VC | 27 | Phil. | 3 yr | MR, alopecia, arthritis, OU, fatigue, panniculitis, fever, headache, myalgia, leukocytopenia, (+) FANA, (+) anti-DNA | Arthritis, fatigue, alopecia headache, fever |
| MN | 42 | C | 11 mo | LCV, arthritis, myalgia, fever, fatigue, (+) FANA, (+) anti-DNA, low C3 C4 | Arthralgia, myalgia, fatigue, headache |
| PD | 42 | C | 3 yr | MR, arthritis, alopecia, OU, (+) FANA, (+) anti-DNA | Arthralgia, MR, OU, fever, fatigue |
| MD | 33 | C | 8 mo | Arthritis, myalgias, MR, (+) FANA | Arthralgia |
| WM | 31 | B | 10 yr | Membranous GN, LAN, s/p stroke, seizures, leukopenia, (+) FANA | LAN, proteinuria |
| LG | 44 | H | 21 mo | MR, OU, PS, RP, alopecia vitiligo, arthritis, myalgia, SS, proteinuria, anemia, (+) FANA, (+) SSA, (+) anti-RNP | MR, OU, PS, RP, alopecia, vitiligo, arthritis, myalgia, SS, proteinuria |
| JS | 48 | C | | Thrombocytopenia, arthritis, alopecia, hypocomplementemia (+) FANA | |
| EH | | C | 9 yr | Vasculitis, MR, anemia, thrombocytopenia (+) FANA | Vasculitic skin lesions |
| LE | 49 | C | | Arthritis, alopecia, MR, OU, anemia, (+) FANA | Arthralgia, fatigue |
| KW | 32 | C | 9 yr | MR, OU, RP, fever, arthritis, myalgia, SS, stroke, pericarditis, costochondritis, (+) FANA | Arthralgia, myalgia, fever, fatigue, MR |
| SM | 26 | C | 3 yr | Mesangial GN, nephrotic syndrome, arthritis, MR, fever, fatigue, (+) FANA | Nephrotic syndrome, arthralgia, fatigue |
| LA | 27 | C | 8 yr | MR, LAN, fever, arthritis, SS, mesangial nephritis, proteinuria, CNS, (+) FANA | Arthritis, costochondritis, fever, fatigue, LAN |

Legend:
MR—malar rash RP—Raynaud's phenomenon OU—oral ulcers SS—sicca syndrome LAN—lymphadenopathy PS—Photosensitivity CNS—CNS involvement

TABLE 2

Summary of outcome measures.

|  | Improved | Worsened | Same |
|---|---|---|---|
| At 3 months (n = 15): |  |  |  |
| SLE-DAI score | 9 | 5 | 1 |
| Physician OA | 10 | 2 | 3 |
| Patient OA | 7 | 4 | 4 |
| ESR | 2 | 2 | 11 |
| Corticosteroid dose (n = 8) | 7 | 0 | 1 |
| At 5–6 months (n = 7): |  |  |  |
| SLE-DAI score | 4 | 1 | 0 |
| Physicians OA | 5 | 2 | 0 |
| Patient OA | 5 | 1 | 1 |
| ESR | 0 | 1 | 6 |
| Corticosteroid dose | 4 | 0 | 0 |

SLE-DAI was scored as improved/worsened if the change was 10% or greater.
Physician OA was scored as improved/worsened if the change was 10% or greater.
Patient OA was scored as improved/worsened if the change was 20% or greater.
ESR was scored as improved/worsened only if values were outside the normal range, and change was 20% or greater.
Corticosteroid dose was scored as improved/worsened if the change was 20% or greater.

TABLE 3

Tolerance and side effects.

DHEA was overall well tolerated.
Side effects included:

*Acneiform Dermatitis* in 8/15 patients (53%).
3 of these patients regarded this as significant, and for one it was grounds for discontinuation of DHEA.
Hirsutism in 2 patients (13%).
Increase in libido in 1 patient (7%), transient (<2 weeks).
Change in taste perception in 1 patient (7%), transient (<2 weeks).
Striae in 1 patient (13%).
Insomnia in 1 patient (7%), transient (<2 weeks).
No changes in menstrual cycle were reported.

TABLE 4

Medication profiles.

8 patients were on corticosteroids at time of entry (average dose 18.3 mg/day of prednisone or equivalent).
At 3 months, the dose was reduced in 7 and unchanged in 1 (average dose 12.4 mg/day of prednisone or equivalent).
8 patients were on anti-malarials at time of entry (hydroxychloroquine/7, quinacrine/1). This was unchanged at 3 months.
4 patients were on Azathioprine at time of entry (average dose 87.5 mg/day).
At 3 months, azathioprine had been discontinued in one patient, the dose was unchanged in 3, and one additional patient had been started on it.

It is evident from the above results, that treatment with DHEA or metabolite of patients with systemic lupus erythematosus provides for substantial improvements in the general well-being of the patient, while allowing for the reduction in other drugs which have serious side effects. Thus, one can reduce the use of glucocorticosteroids so as to substantially diminish the side effects associated with these compounds.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating the symptoms of systemic lupus erythematosis (SLE) in a patient in need of treatment for SLE, said method comprising:

administering to said patient a therapeutic dosage of dehydroepiandrosterone or its sulfate ester, and by said administering, improving said patient's symptoms of SLE, as evidenced by an improvement in SLE-disease activity index score (SLE-DAI).

2. The method of claim 1, wherein said therapeutic dosage is administered in multiple doses.

3. The method of claim 1, wherein said administering is over a period of at least 3 months.

4. The method of claim 1, wherein said administering is via an oral route.

5. The method of claim 1, wherein said effective dosage is in the range of 50–250 mg/day.

6. The method of claim 1, wherein said method further includes administering to said patient a second drug selected from the group consisting of a non-steroidal anti-inflammatory drug, a glucocorticosteroid and an anti-malarial drug.

7. A method of improving the condition of a patient suffering from symptoms of systemic lupus erythematosis (SLE), as evidenced by an improvement in SLE-disease activity index score (SLE-DAI), comprising, administering to the patient, multiple doses of dehydroepiandrosterone or its sulfate ester.

8. The method of claim 7, wherein said multiple doses comprise between 50–250 mg/day.

9. The method of claim 7, wherein said administering is carried out for at least three months.

* * * * *